(12) United States Patent
Kim (10) Patent No.: US 10,933,229 B2
(45) Date of Patent: Mar. 2, 2021

(54) FACIAL SKIN CARE DEVICE AND OPERATION METHOD THEREFOR

(71) Applicant: Jung Kuk Kim, Gyeonggi-do (KR)

(72) Inventor: Jung Kuk Kim, Gyeonggi-do (KR)

(73) Assignee: MYONGJI UNIVERSITY INDUSTRY AND ACADEMIA COOPERATION FOUNDATION, Yongin-si (KR)

( * ) Notice: Subject to any disclaimer, the term of this patent is extended or adjusted under 35 U.S.C. 154(b) by 418 days.

(21) Appl. No.: 15/754,956

(22) PCT Filed: Aug. 26, 2016

(86) PCT No.: PCT/KR2016/009512
§ 371 (c)(1),
(2) Date: Apr. 25, 2018

(87) PCT Pub. No.: WO2017/034368
PCT Pub. Date: Mar. 2, 2017

(65) Prior Publication Data
US 2020/0254243 A1 Aug. 13, 2020

(30) Foreign Application Priority Data
Aug. 27, 2015 (KR) .................. 10-2015-0120923

(51) Int. Cl.
*A61N 1/04* (2006.01)
*A61N 1/36* (2006.01)
*A61N 1/05* (2006.01)
*A61N 1/32* (2006.01)
*A61N 5/06* (2006.01)
*A61N 7/00* (2006.01)

(52) U.S. Cl.
CPC ............. *A61N 1/04* (2013.01); *A61N 1/0548* (2013.01); *A61N 1/328* (2013.01); *A61N 1/3603* (2017.08); *A61N 5/0616* (2013.01); *A61N 7/00* (2013.01); *A61N 2005/0645* (2013.01); *A61N 2005/0651* (2013.01); *A61N 2007/0034* (2013.01)

(58) Field of Classification Search
CPC ..... A61N 1/328; A61N 1/0548; A61N 1/0526
See application file for complete search history.

(56) References Cited

U.S. PATENT DOCUMENTS

| 2008/0082131 | A1* | 4/2008 | Llanos | A61N 1/0548 607/2 |
| 2014/0172041 | A1* | 6/2014 | Draghici | A61B 5/4848 607/45 |
| 2016/0096014 | A1* | 4/2016 | Ajiki | A61C 19/066 433/32 |

FOREIGN PATENT DOCUMENTS

| JP | 02-126863 A | 5/1990 |
| JP | 08-052224 A | 2/1996 |

(Continued)

*Primary Examiner* — George R Evanisko
(74) *Attorney, Agent, or Firm* — Nelson Mullins Riley & Scarborough LLP; Kongsik Kim, Esq.

(57) ABSTRACT

A facial skin care device and a method of operating the same are disclosed. The facial skin care device comprises an oral insertion module configured to have a structure inserted in an oral cavity and include one or more oral electrodes contacted with a skin in the oral cavity, and a main body configured to include a main electrode connected electrically to at least one of the oral electrode on an outer surface of a facial skin and a current generation unit which is connected to the main electrode and generates current for applying electrical stimulation to the facial skin.

17 Claims, 11 Drawing Sheets

(56) References Cited

FOREIGN PATENT DOCUMENTS

| | | |
|---|---|---|
| JP | 2014-158607 A | 9/2014 |
| KR | 20-0389849 Y1 | 7/2005 |
| KR | 10-2011-0130788 A | 12/2011 |
| KR | 10-2012-0029888 A | 3/2012 |

* cited by examiner

FACIAL SKIN CARE DEVICE AND OPERATION METHOD THEREFOR

PRIORITY

This application claims priority under 35 U.S.C. § 119(a) to a Korean patent application filed on Aug. 27, 2015 in the Korean Intellectual Property Office and assigned Serial No. 10-2015-0120923 and a PCT application PCT/KR2016/009512 filed on Aug. 26, 2016, the entire disclosure of which is incorporated herein by reference.

BACKGROUND

Field of the Invention

The present disclosure relates generally to a facial skin care device and a method of operating the same.

Description of the Related Art

Presently, personal devices and devices for specialized skin care shop, for applying stimulation to a skin by using electricity, ultrasonic waves, light and so on, have been widely used.

It is known that applying stimulation to the skin by using electricity, ultrasonic waves, light, etc. affects the synthesis or the regeneration of elastin, chain structure of elastin which is protein for providing skin elasticity, and collagen, fibrillar connective tissue, that are main factors for skin health and skin beauty, and thus, the stimulations have been a subject of intense study. Specially, it is also known that electrical stimulation increases hydroxyproline, a main component of collagen, which stabilizes collagen by forming a helical structure, and enhances collagenesis ability for skin wound.

Recently, non-surgical devices used at home or a specialized skin care shop have been using ultrasonic waves, a light emitting diode (LED) or microcurrent.

Ultrasonic stimulation as a non-invasive treatment method provides sound wave of higher than audible frequency to skin tissue through water soluble gel, and generates thermal effect and non-thermal effect. Ultrasonic thermal effect means increasing temperature of local skin tissue up to 40~45° C. which is the temperature for promoting collagenesis. Non-thermal effect indicates promoting transmittance of cell membrane and calcium intake by inducing cavitation for generating micro-bubbles in blood, lymph and body fluid, thereby promoting collagenesis.

LED stimulation is one of light treatment techniques using energy considerably lower compared to intense pulsed light IPL, and uses LEDs for generating a blue light for removing propionibacterium which is cause of a pimple, a yellow light or an orange light for promoting collagenesis or a red light for reducing infection and promoting treatment, and so on.

Usage of microcurrent has continuously increased in medical field or skin care field. The microcurrent keeps tension of skin muscle and provides vitality to the skin by promoting blood circulation. Additionally, the microcurrent strengthens facial muscles by exercising the facial muscles, thereby maintaining facial skin tightly.

Most of devices used presently apply ultrasonic waves or LED light in a direction from skin surface to inside of the skin. Specially, in the event that the microcurrent is applied to the skin, the microcurrent flows transvesically on the facial muscle between two electrodes contacted with the facial skin, and thus it can't be delivered deeply to the facial skin muscle. As a result, the microcurrent may not flow in the same direction as the elastin or the collagen chain structure but flow in a side direction, and so effect due to the microcurrent is reduced.

SUMMARY

An aspect of the invention provides a facial skin care device and a method of operating the same, for outputting ultrasonic waves and an LED light in a direction from inside of an oral cavity to outside of a facial skin and making microcurrent flow through a facial skin in a direction from outside of the facial skin to inside of the facial skin or a direction from the inside of the facial skin to the outside of the facial skin.

In one aspect, a facial skin care device is disclosed.

A facial skin care device according to one embodiment of the invention comprises an oral insertion module configured to have a structure inserted in an oral cavity and include one or more oral electrodes contacted with a skin in the oral cavity; and a main body configured to include a main electrode connected electrically to at least one of the oral electrode on an outer surface of a facial skin and a current generation unit which is connected to the main electrode and generates current for applying electrical stimulation to the facial skin.

The main body further includes a wave generation unit connected to the main electrode and configured to generate a wave for measuring impedance between the main electrode and the oral electrodes; and an impedance measuring unit configured to measure impedance for each of the oral electrodes by current passing through a high pass filter after flowing from the main electrode to each of the oral electrodes through the facial skin.

The wave generation unit includes a circuit for generating one of a sine wave or a square wave, wherein the wave generation unit includes a circuit for generating the square wave so that the wave generation unit has simple structure.

The main body further includes a switch configured to connect at least one of the oral electrodes to the current generation unit; and a switch driving unit configured to deliver a driving signal to the switch.

The main body further includes a control unit for controlling the wave generation unit and the impedance measuring unit so that the wave generation unit and the impedance measuring unit measure the impedance for each of the oral electrodes, selecting at least one of the oral electrodes according to the measured impedance, and controlling the switch driving unit so that current flows through the selected oral electrode, when a measurement mode is selected as an operation mode.

The control unit selects an oral electrode nearest or farthest to the main electrode or an oral electrode corresponding to impedance set by a user, by using the measured impedance.

The control unit controls the switch driving unit so that current flows through every oral electrode, when a whole operation mode is selected as the operation mode.

The control unit selects at least one oral electrode adjacent to a specific skin portion and controls the switch driving unit so that current flow through the selected oral electrode, when a specific skin stimulation mode for treating the specific skin portion is selected as the operation mode.

The main body further includes an auxiliary electrode connected electrically to the main electrode on the outer surface of the facial skin, wherein the switch connects the auxiliary electrode to the current generation unit according to the driving signal of the switch driving unit, and the control unit controls the switch driving unit so that current flows from the main electrode to the auxiliary electrode, when a skin operation mode is selected as the operation mode.

The main electrode and the auxiliary electrode have different height so that the auxiliary electrode is not contacted with the facial skin when the main electrode is electrically connected to the oral electrode with contacted with the facial skin.

The oral insertion module has mouthpiece shape.

The oral insertion module further includes a plurality of LED light sources contacted with the skin in the oral cavity, wherein the main body further includes an LED driving unit for driving at least one of the LED light sources.

The oral insertion module further includes a plurality of ultrasonic vibrators contacted with the skin in the oral cavity, wherein the main body further includes an ultrasonic wave generation unit for generating ultrasonic waves through at least one of the ultrasonic vibrators.

In another aspect, a facial skin care device is disclosed.

A facial skin care device according to anther embodiment of the invention comprises a main electrode contacted with an outer surface of a facial skin; and a current generation unit connected to the main electrode and configured to generate current for applying electrical stimulation to the facial skin. Here, the main electrode is electrically connected to at least one of the oral electrodes contacted with a skin in an oral cavity.

In still another aspect, a facial skin care device is disclosed.

A facial skin care device according to still another embodiment of the invention comprises at least one oral electrode inserted in an oral cavity and contacted with a skin in an oral cavity. Here, electrical stimulation is applied to the facial skin according as at least one of the oral electrodes is electrically connected to a main electrode contacted with an outer surface of a facial skin.

In still another aspect, a method of operating a facial skin care device is disclosed.

A method of operating a facial skin care device according to one embodiment of the invention comprises connecting respectively electrodes to an outer surface of a facial skin and a skin in an oral cavity; and applying a power to the electrodes so that current flows from the outer surface to the skin in the oral cavity or from the skin in the oral cavity to the outer surface.

The step of applying the power comprises receiving selection of an operation mode; measuring impedance between a main electrode contacted with the outer surface of the facial skin and an oral electrode contacted with the skin in the oral cavity when a measurement mode is selected; connecting an oral electrode selected according to the measured impedance to a current generation unit connected to the main electrode; and generating current through the current generation unit.

The step of connecting the oral electrode includes selecting an oral electrode nearest or farthest to the main electrode or an oral electrode corresponding to impedance set by a user, depending on the measured impedance.

The step of applying the power includes connecting every oral electrode to the current generation unit when a whole operation mode is selected.

The step of applying the power includes connecting at least one oral electrode adjacent to a specific skin portion to the current generation unit when a preset specific skin stimulation mode for treating the specific skin portion is selected.

A facial skin care device of the invention may stimulate efficiently inner muscle of a facial skin by outputting ultrasonic waves and an LED light in a direction from inside of an oral cavity to outside of the facial skin. The facial skin care device may make microcurrent flow through the facial skin in a direction from the outside of the facial skin to inside of the facial skin or a direction from the inside of the facial skin to the outside of the facial skin so that the microcurrent flows in the same vertical direction as chain structure of elastin and collagen, thereby increasing regeneration of skin muscle and skin care effect by electrical stimulation.

DETAILED DESCRIPTION

Example embodiments of the invention are disclosed herein. However, specific structural and functional details disclosed herein are merely representative for purposes of describing example embodiments of the invention, however, example embodiments of the invention may be embodied in many alternate forms and should not be construed as limited to example embodiments of the invention set forth herein.

In describing the invention, if it is determined that explanation about relevant published technique blurs important point of the invention, any description about the technique will be omitted. Furthermore, numbers (e.g. first, second, etc.) used in the invention are discernment sign for discriminating one element from another element.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

Hereinafter, various embodiments of the invention will be described in detail with reference to accompanying drawings. Like numbers refer to like elements throughout the description of the figures.

Figure 1:
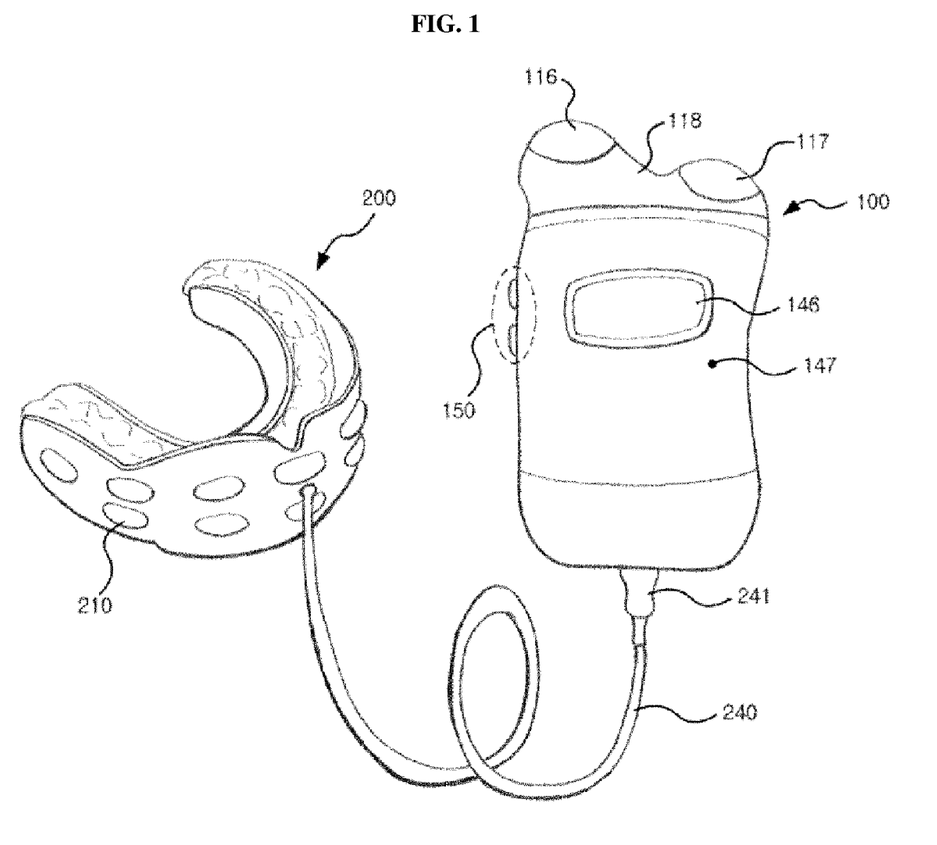
FIG. 1 is a view illustrating schematically appearance of a facial skin care device according to one embodiment of the invention.

FIG. 1 is a view illustrating schematically appearance of a facial skin care device according to one embodiment of the invention.

In FIG. 1, the facial skin care device includes a main body 100 and an oral insertion module 200.

The oral insertion module 200 may have a shape inserted in an oral cavity, e.g. a shape of a mouthpiece shown in FIG. 1, and include a plurality of an oral electrodes 210 and a connection cable 240 connected to the main body 100, the oral electrodes 210 being formed on a surface of the oral insertion module 200 so that they are contacted with a skin in an oral cavity. The connection cable 240 may include a connector 241 formed on its edge part, and be connected to the main body 100 through the connector 241. Of course, the oral insertion module 200 is not limited to have the shape of the mouthpiece shown in FIG. 1, but it may be variously modified as long as the oral electrode 210 can be inserted in the oral cavity to that the oral electrode 210 is located in the oral cavity.

Figure 3:
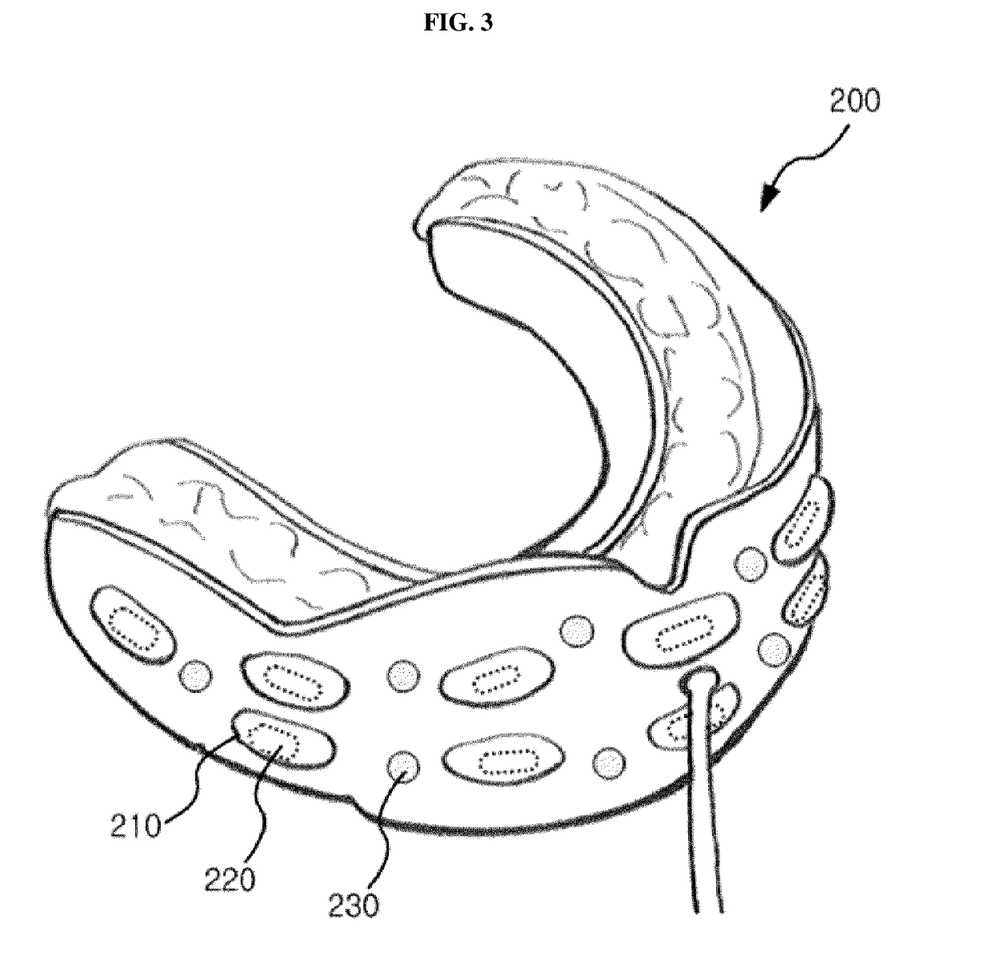
FIG. 3 is a view illustrating an oral insertion module including an oral electrode, a ultrasonic vibrator and an LED light source according to one embodiment of the invention.

The oral insertion module 200 may further includes an ultrasonic vibrator 220 for outputting ultrasonic waves with formed on the surface of the oral insertion module 200 and/or an LED light source 230 other than the oral electrode 210, the ultrasonic vibrator 220 being contacted with the skin in the oral cavity. That is, the oral insertion module 200 may include at least one of the oral electrode 210, the ultrasonic vibrator 220 and the LED light source 230. For example, FIG. 3 shows the oral insertion module including the oral electrode, the ultrasonic vibrator and the LED light source. As shown in FIG. 3, the ultrasonic vibrator 220 may be formed on the same position as the oral electrode 210, and the LED light source 230 may be formed between the oral electrodes 210.

Figure 4:
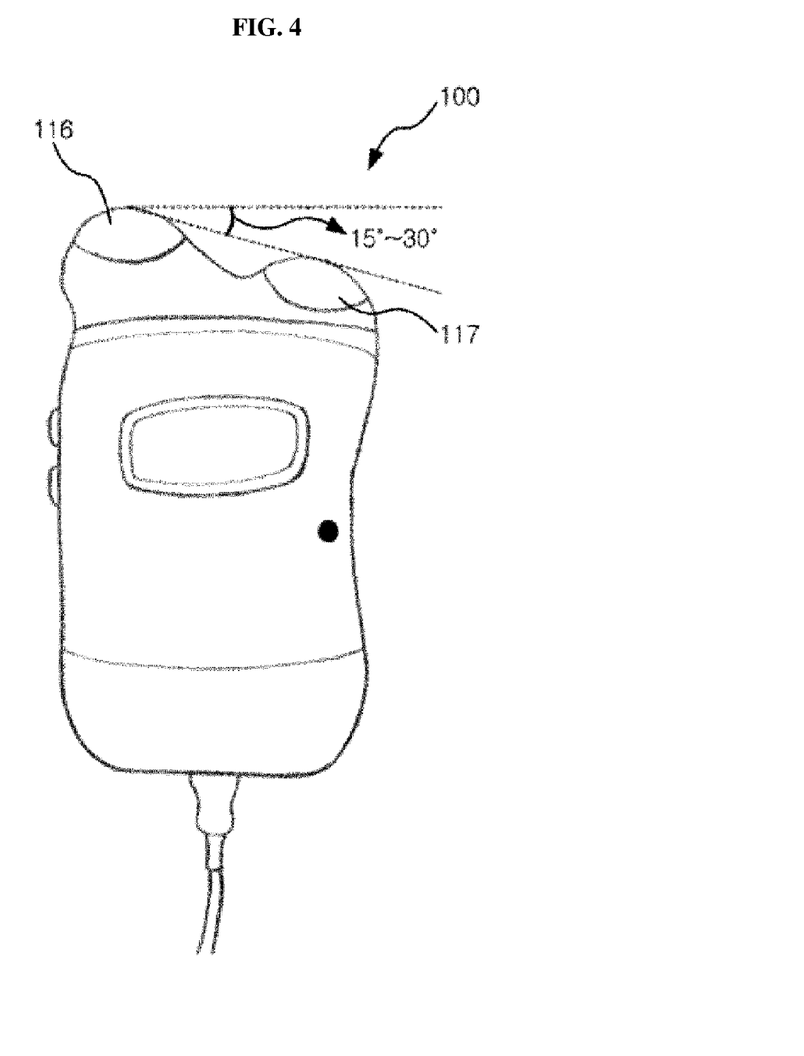
FIG. 4 is a view illustrating the angle formed by the main electrode and the auxiliary electrode according to one embodiment of the invention.

The main body 100 may include a main electrode 116 connected electrically to the oral electrode 210 on an outer surface of a facial skin, an auxiliary electrode 117 connected electrically to the main electrode 116 on the outer surface of the facial skin, a display module 146, a sound output module 147 and an input unit 150. Here, the main electrode 116 and the auxiliary electrode 117 may be electrically separated due to an insulator 118 formed between the main electrode 116 and the auxiliary electrode 117. The main electrode 116 and the auxiliary electrode 117 may have different height so that the auxiliary electrode 117 is not contacted with the facial skin when the main electrode 116 is electrically connected to the oral electrode 210 according as the main electrode 116 is contacted with the facial skin. That is, the main electrode 116 may be formed with greater height than the auxiliary electrode 117 as shown in FIG. 1. For example, in FIG. 4, an angle between a straight line for connecting the main electrode 116 to the auxiliary electrode 117 and a horizontal line may be 15° to 30°. FIG. 4 is a view illustrating the angle formed by the main electrode and the auxiliary electrode according to one embodiment of the invention.

The facial skin care device is schematically described based on its appearance in above description. Hereinafter, the facial skin care device will be described in detail based on elements of the main body 100 and the oral insertion module 200.

Figure 2:
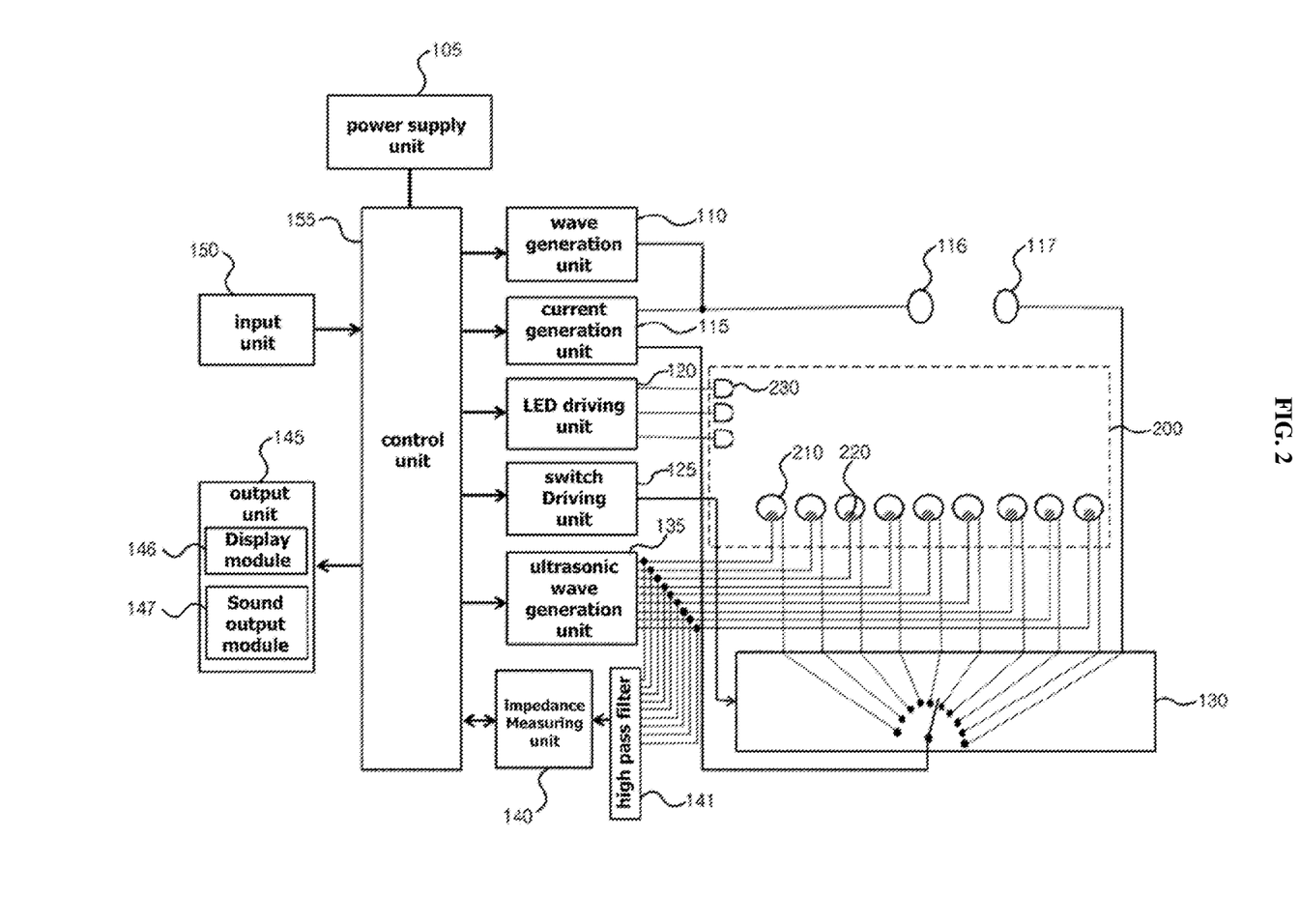
FIG. 2 is a view illustrating schematically a facial skin care device according to one embodiment of the invention.

FIG. 2 is a view illustrating schematically a facial skin care device according to one embodiment of the invention.

In FIG. 2, the main body 100 of the facial skin care device includes a power supply unit 105, a wave generation unit 110, a current generation unit 115, the main electrode 116, the auxiliary electrode 117, an LED driving unit 120, a switch driving unit 125, a switch 130, an ultrasonic wave generation unit 135, an impedance measuring unit 140, an output unit 145, an input unit 150 and a control unit 155.

The oral insertion module 200 of the facial skin care device includes the oral electrode 210, the ultrasonic vibrator 220 and the LED light source 230.

The power supply unit 105 supplies a power to the facial skin care device. For example, the power supply unit 105 may be a disposable battery or a chargeable battery.

The wave generation unit 110 generates a wave for measuring impedance between the main electrode 116 and each of the oral electrodes 210. For example, the wave generation unit 110 may include a circuit for generating one of a sine wave or a square wave with a frequency of 50~500 kHz and amplitude of several μA. In the event of designing a wave generation circuit, a circuit for generating the square wave may have simpler structure than that for generating the sine wave. Accordingly, the wave generation unit 110 may be designed with the circuit for generating the square wave, so as to realize more simple circuit.

The impedance measuring unit 140 measures impedance for each of the oral electrodes 210 by using current passing through the high pass filter 141 after flowing from the main electrode 116 to each of the oral electrodes 210 through the facial skin.

The impedance measurement is for searching an oral electrode 210 nearest or farthest from the main electrode 116 or an oral electrode 210 corresponding to impedance set by a user depending on the measured impedance and making current flow to the searched oral electrode 210.

For example, an oral electrode 210 nearest to the main electrode 116 may have smallest impedance. Thus, the facial skin care device may search an oral electrode 210 having smallest impedance by measuring sequentially the impedance for each of the oral electrodes 210 and make the current flow to the oral electrode nearest to the main electrode 116, when the main electrode 116 moves along the outer surface of the facial skin. As a result, the facial skin care device may increase effect to the facial skin by current flowing through the facial skin in a direction from outside of the facial skin to inside of the facial skin.

For example, a wave for the impedance measurement may be repeatedly generated for 0.001 second whenever 0.1 second in order to reduce consumption of a battery, and the impedance measuring may be performed depending on the wave. Period and time of impedance generation for the impedance measurement may be adjusted depending on setting, and the impedance measurement may be performed by generating sequentially the wave.

The current generation unit 115 generates constant current so that the current flows between the main electrode 116 and the oral electrode 210 to apply electrical stimulation to the facial skin.

For example, the current generation unit 115 may be a constant current source for generating constant current of 0.2 mA to 0.4 mA, and an optimal value of the generated current may be 0.37 mA. The current generation unit 115 may generate preset current irrespective of impedance change between the main electrode 116 and the oral electrode 210. The constant current generated by the current generation unit 115 may flow simultaneously through the main electrode 116 with current having a wave generated by the wave generation unit 110, or stop current generation while the wave for the impedance measurement is generated. The constant current generated by the current generation unit 115 may flow from the main electrode 116 to the current generation unit 115 via the oral electrode 210 connected to the switch 130, or flow from the oral electrode 210 connected to the switch 130 to the current generation unit 115 via the main electrode 116.

The switch driving unit 125 delivers a driving signal to the switch 130 so that at least one of the oral electrodes 210 or the auxiliary electrode 117 is connected to the current generation unit 115.

The switch 130 connects one or more of the oral electrodes 210 and the auxiliary electrode 117 to the current generation unit 115 according to the driving signal of the switch driving unit 125.

For example, the switch driving unit 125 may deliver the driving signal to the switch 130 so that a switch 130 corresponding to an oral electrode 210 selected according to measured impedance between the main electrode 116 and each for the oral electrodes 210 is turned on depending on control of the control unit 155.

The LED driving unit 120 drives the LED light source 230 according to control of the control unit 155. For example, the LED driving unit 120 may drive the LED light source 230 to output light by supplying proper current to the LED light source 230 to be lighted, thereby providing light stimulation for skin care to the facial skin.

The ultrasonic wave generation unit 135 generates ultrasonic waves through the ultrasonic vibrator 220. For example, the ultrasonic wave generation unit 135 may supply a driving signal having higher than audible frequency to the ultrasonic vibrator 220, thereby generating ultrasonic waves in the oral cavity to improve skin elasticity and skin care due to vibration. The ultrasonic wave generation unit 135 may stop generation of the ultrasonic waves when the impedance is measured.

The output unit 145 outputs a signal or data generated according to various operations executed in the facial skin care device. For example, the output unit 145 includes the display module 146 and the sound output module 147 as shown in FIG. 1, and may display a set signal such as an operation mode inputted by the user or usage guide information on the screen, or may generate voice through a speaker.

The input unit 150 receives a signal by the user. For example, the input unit 150 may receive a signal for turning on/off a power of the facial skin care device by a button type switch as shown in FIG. 1, or receive a user selection signal concerning the operation mode.

The control unit 155 controls whole operation of the facial skin care device.

Particularly, the control unit 155 controls the wave generation unit 100 and the impedance measuring unit 140 so that the wave generation unit 110 and the impedance measuring unit 140 measure impedance for each of the oral electrodes 210, selects at least one of the oral electrodes 210 according to the measured impedance, and drives the switch driving unit 125 so that constant current flows through the selected oral electrode 210. Here, the control unit 155 may select the oral electrode 210 nearest or farthest to the main electrode 116 or the oral electrode 210 corresponding to impedance set by the user, depending on the user's setting.

Hereinafter, skin muscle strengthening effect or facial skin care effect of the facial skin care device will be described with reference to accompanying drawings FIG. 5 to FIG. 8.

Figure 5:
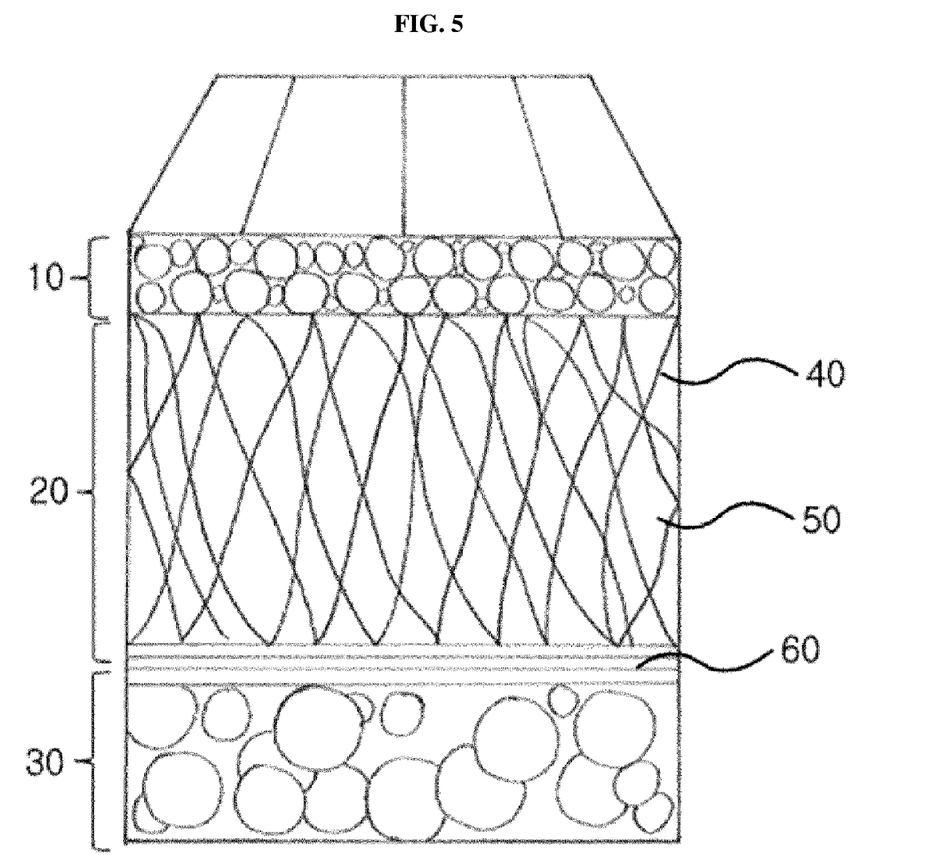
FIG. 5 is a sectional view illustrating healthy skin.

FIG. 5 is a sectional view illustrating healthy skin.

In FIG. 5, the skin includes the epidermis 10, the dermis 20 and the hypodermis 30. Specially, elastin 40 which is high elastic protein in a connective tissue of a mammal, collagen 50 with chain structure which is fibrillar connective tissue located below epidermis of a vertebrate and a capillary 60 for supplying blood to the skin exist in the dermis 20. It is well known that the elastin 40 and the collagen 50 are main factor for skin elasticity and skin care.

Figure 6:
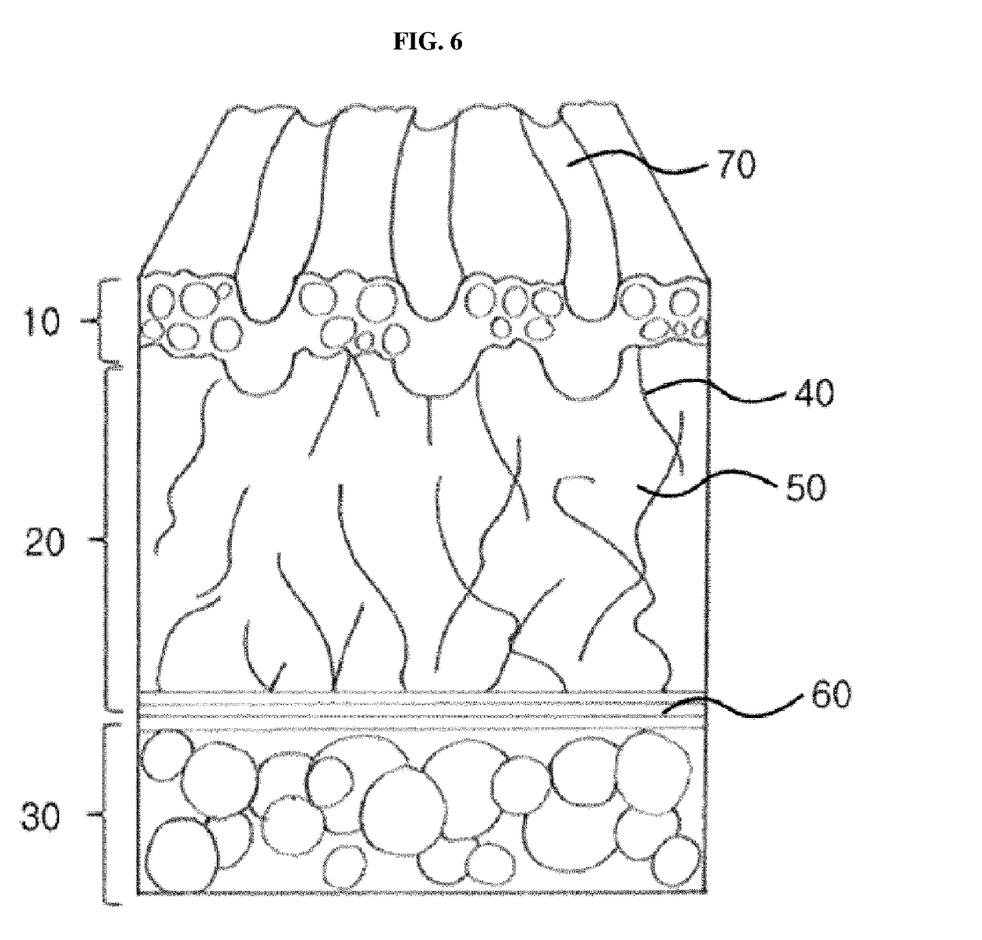
FIG. 6 is a sectional view illustrating an aged skin.

FIG. 6 is a sectional view illustrating an aged skin.

In the aged skin shown in FIG. 6, unlike the healthy skin, chain structure of elastin and the collagen 50 is broken or is not stood normally, and a wrinkle 70 generated by aging or damage of the skin is shown together.

Figure 7:
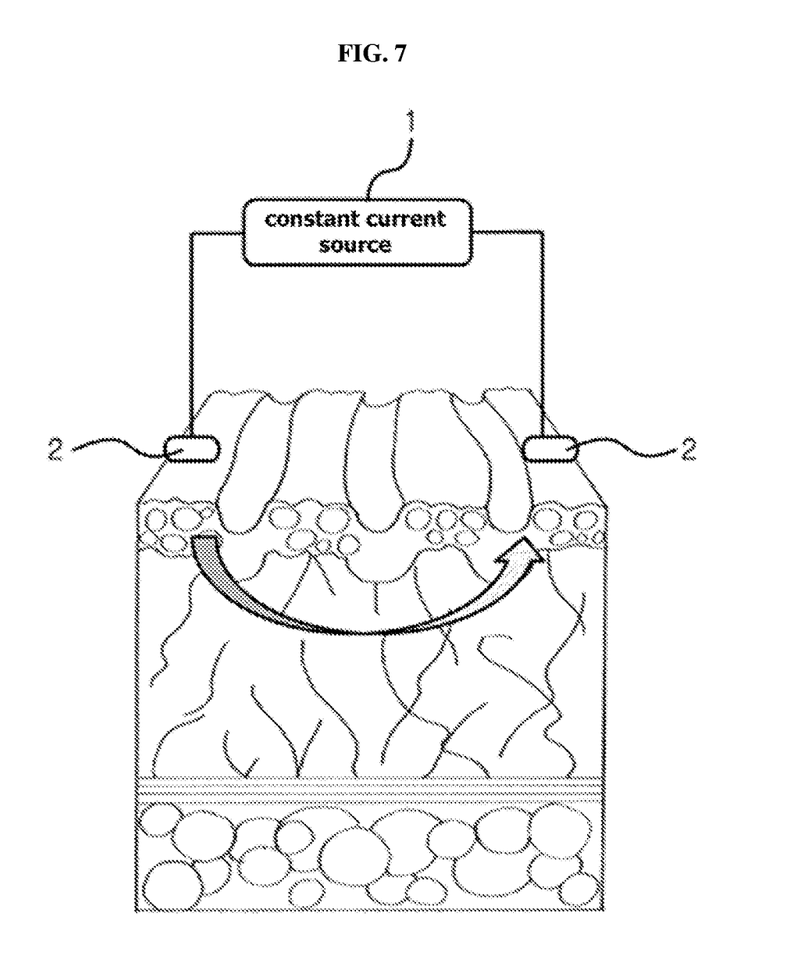
FIG. 7 is a view illustrating conventional electrical stimulation method.

FIG. 7 is a view illustrating conventional electrical stimulation method.

In FIG. 7, two electrodes 2 locates on a surface of a skin in conventional method, and thus constant current flows horizontally along near surface of an aged skin between the electrodes 2 when the constant current generated by a constant current source 1 flows through the electrodes 2. In this case, the constant current flows in a direction different from a direction of chain structure of damaged elastin 40 and collagen 50 and it is not deeply flowed in the skin, and so it is difficult to achieve sufficiently skin muscle strength effect or skin care effect by electrical stimulation.

Figure 8:
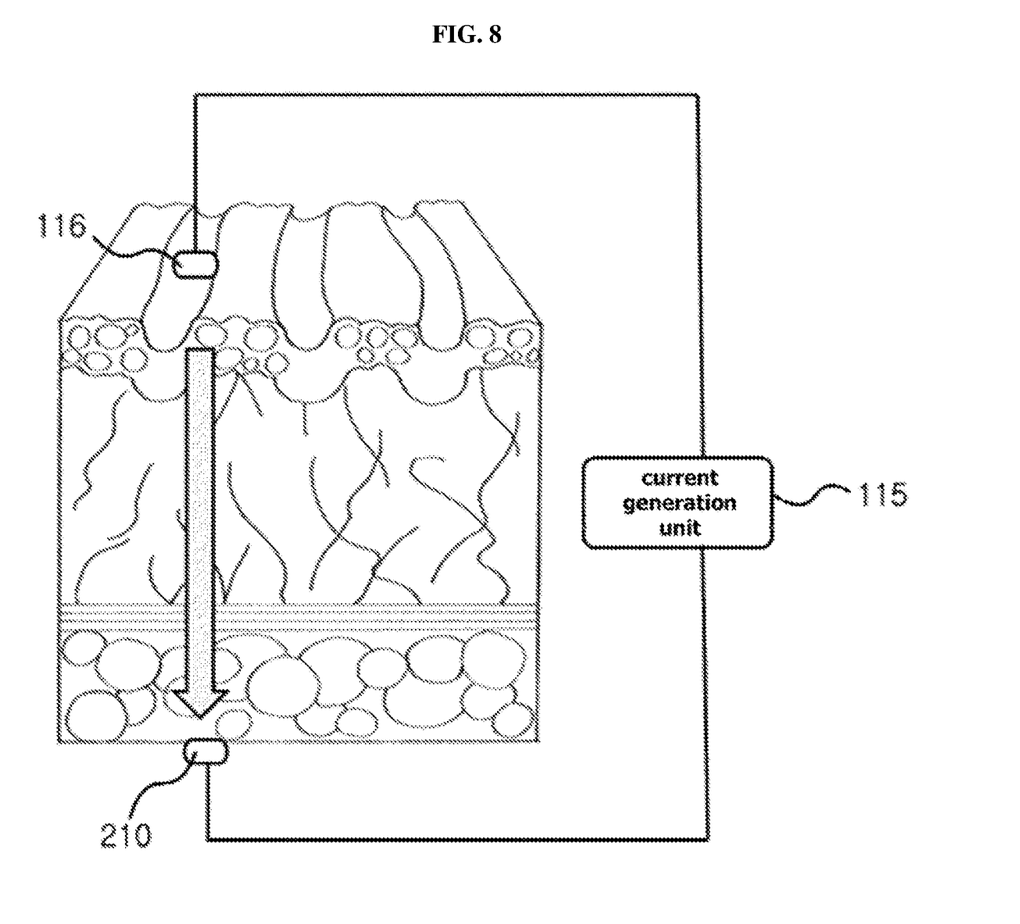
FIG. 8 is a view illustrating an electrical stimulation method according to one embodiment of the invention.

FIG. 8 is a view illustrating an electrical stimulation method according to one embodiment of the invention.

The problem of the convention method shown in FIG. 7 may be solved by providing electrical stimulation to the facial skin using the oral electrode 210 formed on the surface of the oral insertion module 200 inserted in the oral cavity and the main electrode 116 contacted with the outer surface of the facial skin as shown in FIG. 8.

That is, the constant current generated by the current generation unit 115 may flow vertically through the facial skin according as it flows through the oral electrode 210 and the main electrode 116, as shown in FIG. 8.

Accordingly, the constant current may flow deeply in the skin in the same direction as the chain structure of damaged elastin 40 and collagen 50, and thus the electrical stimulation may be sufficiently applied to the chain structure of the elastin 40 and the collagen 50 and the skin muscles.

Hereinafter, the control unit 155 of the facial skin care device in FIG. 2 will be described.

For example, the control unit 155 may control elements of the facial skin care device according to a measurement mode, for selecting at least one of the oral electrodes 210 depending on the measured impedance for each of the oral electrodes 210, a whole operation mode for selecting every oral electrode 210 and a skin operation mode for selecting the auxiliary electrode 117. This will be described with reference to accompanying drawings FIG. 9 to FIG. 12.

FIG. 9 to FIG. 12 are views illustrating operation modes of the facial skin care device.

Figure 9:
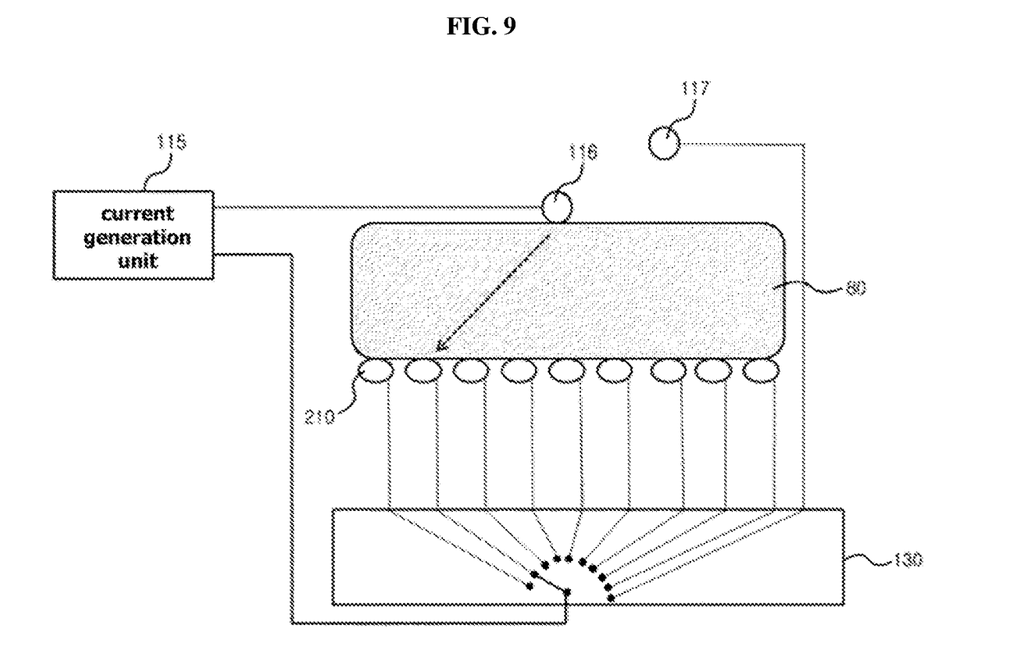
FIG. 9 to FIG. 12 are views illustrating operation modes of the facial skin care device.
Figure 10:
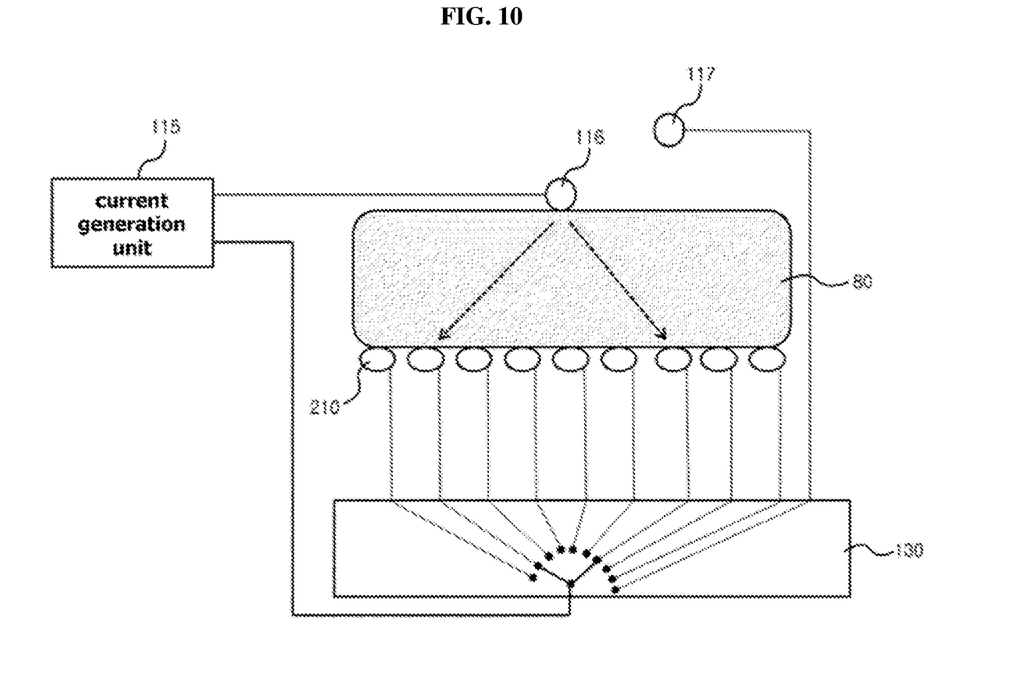

In FIG. 9 and FIG. 10, the control unit 155 may select one or two of the oral electrodes 210 by using the measured impedance for each of the oral electrodes 210, when the measurement mode is selected as the operation mode. Here, the control unit 155 may select the oral electrode 210 nearest or farthest from the main electrode 116, or the oral electrode 210 corresponding to impedance set by the user, depending on the user's setting.

The control unit 155 may control the switch 130 and the current generation unit 115 so that the switch 130 connects the current generation unit 115 to the selected oral electrode 210 and the current generation unit 115 generates the constant current and thus the constant current flows from the main electrode 210 to the selected oral electrode 210 through the facial skin 80.

Figure 11:
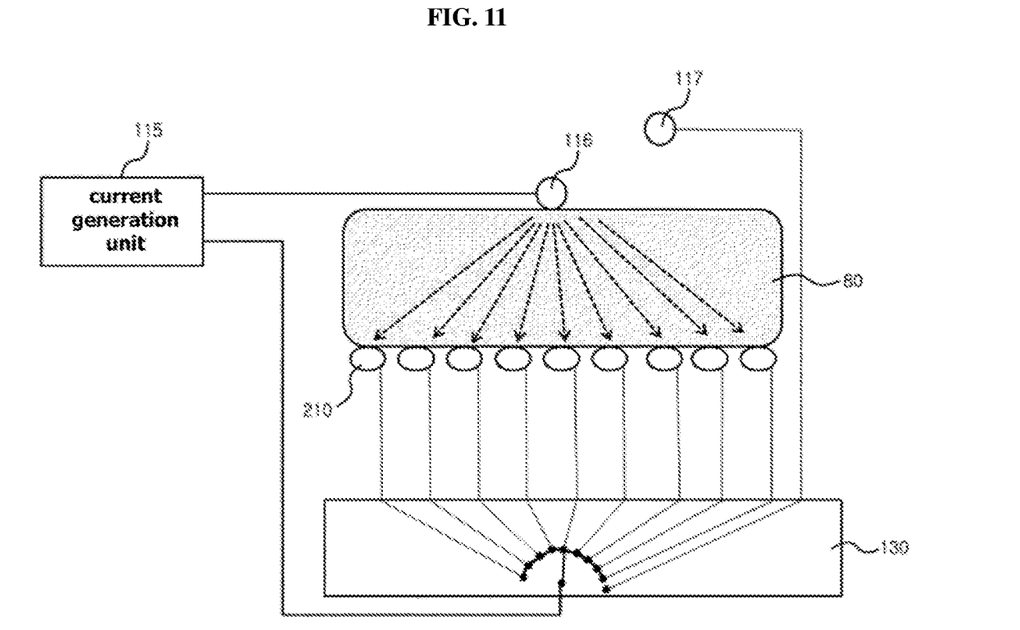

In FIG. 11, the control unit 155 may control the switch 130 and the current generation unit 115 so that every oral electrode 210 is selected, the switch 130 connects the current generation unit 115 to every oral electrode 210 and the current generation unit 115 generates the constant current, and thus the constant current flows from the main electrode 116 to the every oral electrode 210 through the facial skin 80, when the whole operation mode is selected as the operation mode.

Figure 12:
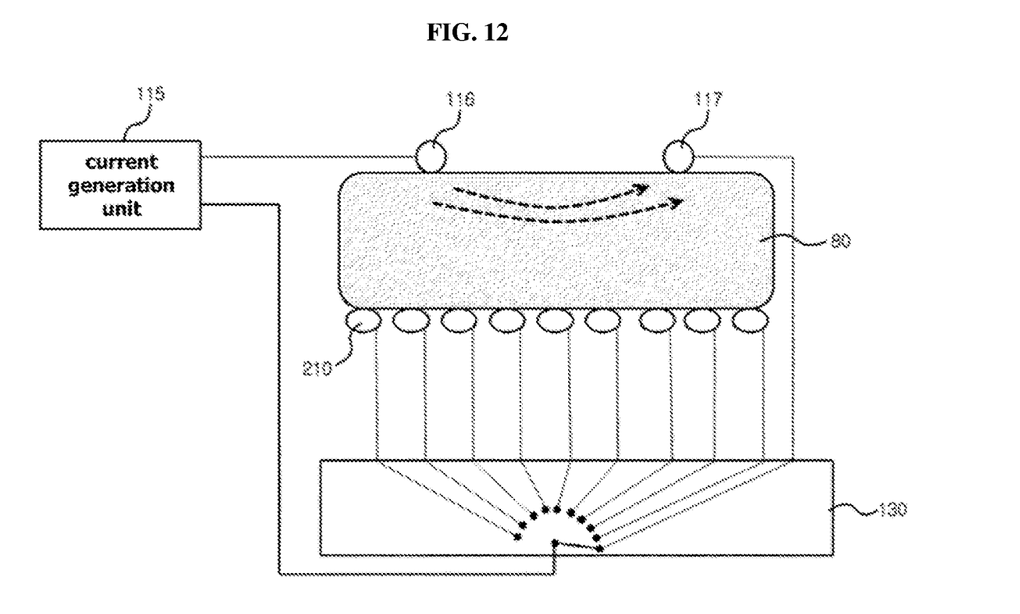

In FIG. 12, the control unit 155 may control the switch 130 and the current generation unit 115 so that the auxiliary electrode 117 is selected, the switch 130 connects the current generation unit 115 to the auxiliary electrode 117 and the current generation unit 115 generates the constant current and thus the constant current flows from the main electrode 116 to the auxiliary electrode 117, when the skin operation mode is selected as the operation mode.

In another embodiment, the operation mode may further include a specific skin stimulation mode for treating a preset specific skin portion. That is, the control unit 155 may select at least one oral electrode 210 capable of applying intensively electrical stimulation to the specific skin portion and control the switch 130 and the current generation unit 115 so that the switch 130 connects the current generation unit 115 to the selected oral electrode 210 and the current generation unit 115 generates the constant current and thus the constant current flows from the main electrode 116 to the selected oral electrode 210 through the specific skin portion, when the specific skin stimulation mode is selected as the operation mode.

For example, at least one oral electrode 210 adjacent to wrinkle on the facial skin 80 may be selected, and the electrical stimulation may applied intensively to the wrinkle through the selected oral electrode 210, when a treatment for improving the wrinkle is performed.

Figure 13:
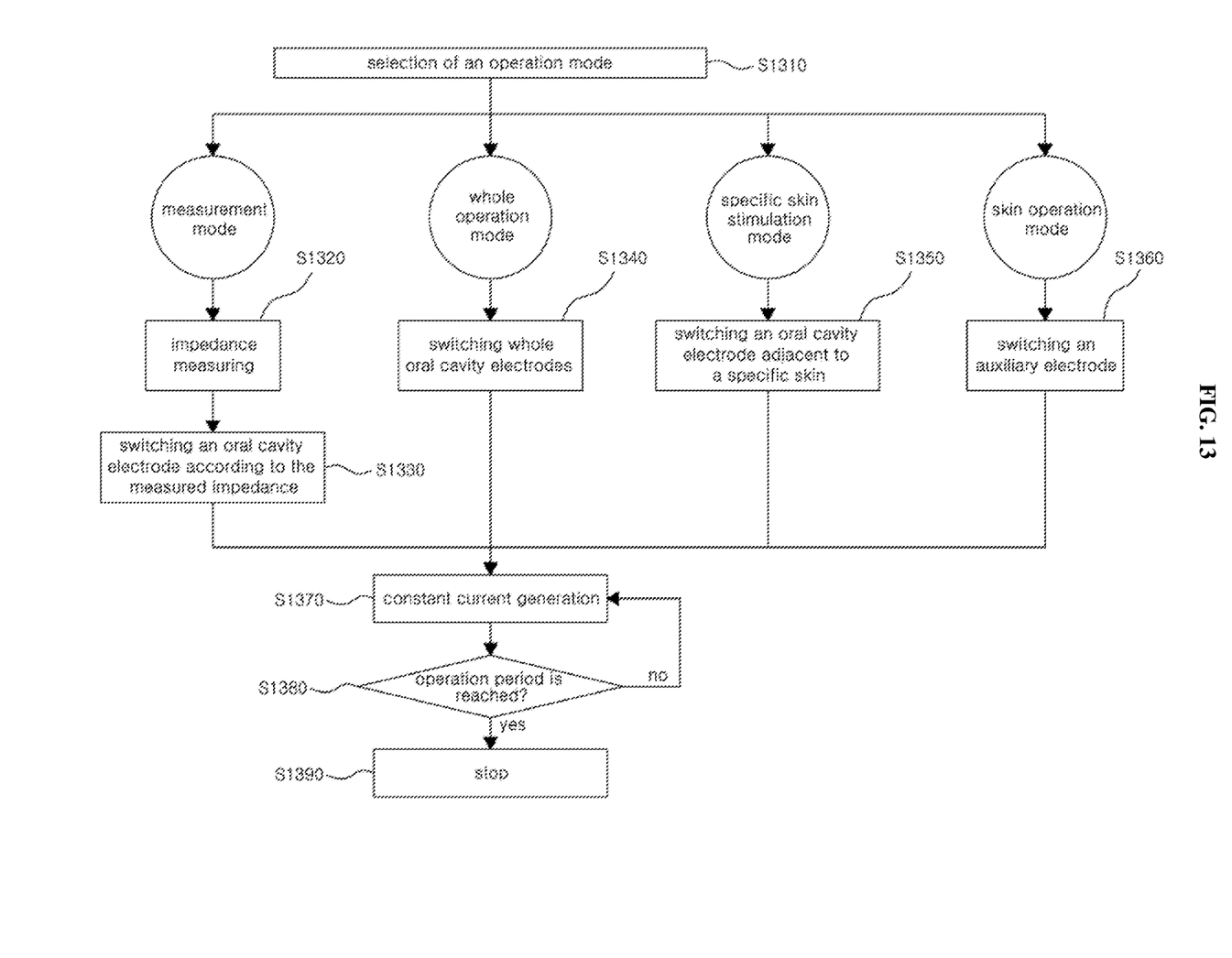
FIG. 13 is a flowchart illustrating operation of the facial skin care device according to one embodiment of the invention.

FIG. 13 is a flowchart illustrating operation of the facial skin care device according to one embodiment of the invention.

In a step of S1310, the facial skin care device receives selection of the operation mode. Here, the operation mode may include the measurement mode, for selecting at least one of the oral electrodes 210 depending on the measured impedance for each of the oral electrodes 210, the whole operation mode for selecting every oral electrode 210 and the skin operation mode for selecting the auxiliary electrode 117.

In a step of S1320, the facial skin care device measures impedance of each of the oral electrodes 116 when the measurement mode is selected. For example, the facial skin care device generates a wave for measuring impedance between the main electrode 116 and each of the oral electrodes 210, and then measures the impedance for each of the oral electrodes 210 by using current passing through the high pass filter 141 after flowing through each of the oral electrodes 210 from the main electrode 116.

In a step of S1330, the facial skin care device switches selectively the oral electrodes 210 according to the measured impedance for each of the oral electrodes 210. For example, the facial skin care device may switch selectively the oral electrodes 210 so that the constant current flows through the oral electrode 210 nearest or farthest to the main electrode 116 or the oral electrode 210 corresponding to the impedance set by the user, depending on the user's setting.

In a step of S1340, the facial skin care device turns on every switch 130 connected to every oral electrode 210 so that constant current flows through every oral electrode 210, when the whole operation mode is selected.

In a step of S1350, the facial skin care device switches selectively at least one oral electrode 210 adjacent to preset specific skin portion, so as to apply intensively electrical stimulation to the specific skin portion, when the specific skin stimulation mode is selected. For example, the facial skin care device may switch selectively at least one oral electrode 210 adjacent to wrinkle, in case of applying intensively electrical stimulation to the wrinkle.

In a step of S1360, the facial skin care device switches selectively the auxiliary electrode 117 so that constant current flows through the auxiliary electrode 117, when the skin operation mode is selected.

In a step of S1370, the facial skin care device generates constant current. The generated constant current may provide electrical stimulation to the facial skin 80 by flowing from the main electrode 116 to at least one of the oral electrodes 210 or the auxiliary electrode 117.

In a step of S1380, the facial skin care device determines whether or not preset operation period reaches.

In a step of S1390, the facial skin care device stops its operation when the operation period reaches.

The method of operating the facial skin care device of the invention can be implemented in the form of program instructions that may be performed using various computer means and can be recorded in a computer-readable medium. Such a computer-readable medium can include program instructions, data files, data structures, etc., alone or in combination.

The program instructions recorded on the medium can be designed and configured specifically for the present invention or can be a type of medium known to and used by the skilled person in the field of computer software. Examples of a computer-readable medium may include magnetic media such as hard disks, floppy disks, magnetic tapes, etc., optical media such as CD-ROM's, DVD's, etc., magneto-optical media such as floptical disks, etc., and hardware devices such as ROM, RAM, flash memory, etc. Examples of the program of instructions may include not only machine language codes produced by a compiler but also high-level language codes that can be executed by a computer through the use of an interpreter, etc.

The hardware mentioned above can be made to operate as one or more software modules that perform the actions of the embodiments of the invention, and vice versa.

The embodiments of the invention described above are disclosed only for illustrative purposes. A person having ordinary skill in the art would be able to make various modifications, alterations, and additions without departing from the spirit and scope of the invention, but it is to be appreciated that such modifications, alterations, and additions are encompassed by the scope of claims set forth below.

What is claimed is:

1. A facial skin care device comprising:
    an oral insertion module configured to be inserted in an oral cavity, the oral insertion module including one or more oral electrodes configured to contact a membrane in the oral cavity; and
    a main body that comprises:
        a main electrode configured to contact an outer surface of a facial skin;
        a current generation unit that is electrically connected to the main electrode and the one or more oral electrodes, the current generation unit generating current for applying electrical stimulation to the facial skin;

switches, each of which being connected to an oral electrode among the one or more oral electrodes to switchingly connect the respective oral electrode to the current generation unit;

a switch driving unit that generates a driving signal to operate the switches; and an auxiliary electrode configured to contact the outer surface of the facial skin, the auxiliary electrode being electrically connected to the current generation unit through the switches, wherein modes of operating the facial skin care device include a measurement mode and a skin operation mode, wherein, in the measurement mode, the current flows from the main electrode to at least one oral electrode among the one or more oral electrodes that is selected by the driving signal, and wherein, in the skin operation mode, the current flows from the main electrode to the auxiliary electrode.

2. The facial skin care device of claim 1, wherein the main body further includes:

a wave generation unit connected to the main electrode and configured to generate a wave as the current for measuring impedance between the main electrode and each of the one or more oral electrodes;

a high pass filter; and an impedance measuring unit configured to measure the impedance for the each of the one or more oral electrodes based on the current flowing from the main electrode to the one or more oral electrodes through the facial skin and the high pass filter.

3. The facial skin care device of claim 2, wherein the wave generated by the wave generation unit is a sine wave or a square wave.

4. The facial skin care device of claim 2, wherein the wave generated by the wave generation unit is a square wave.

5. The facial skin care device of claim 2, wherein the main body further includes a control unit, and in the measurement mode, the control unit is configured to:

cause the wave generation unit and the impedance measuring unit to measure the impedance for the each of the one or more oral electrodes;

select at least one oral electrode among the one or more oral electrodes according to the measured impedance; and cause the switch driving unit to allow the current to flow through the selected at least one oral electrode.

6. The facial skin care device of claim 5, wherein the control unit is further configured to select an oral electrode nearest or farthest to the main electrode or an oral electrode corresponding to a user-specified impedance among the one or more oral electrodes, by using the measured impedance.

7. The facial skin care device of claim 5, wherein the modes of operating the facial skin care device further include a whole operation mode, in which the control unit is configured to cause the switch driving unit to allow the current to flow through all of the one or more oral electrodes.

8. The facial skin care device of claim 5, wherein the modes operating the facial skin care device further include a specific skin portion stimulation mode for treating a user-specified skin portion in the facial skin, in which the control unit is configured to:

select at least one oral electrode adjacent to the user-specified skin portion among the one or more oral electrodes; and cause the switch driving unit to allow the current to flow through the selected at least one oral electrode.

9. The facial skin care device of claim 1, wherein the main electrode and the auxiliary electrode have different protruding heights with respect to an outer surface of the main body.

10. The facial skin care device of claim 1, wherein the oral insertion module has a mouthpiece shape.

11. The facial skin care device of claim 1, wherein the oral insertion module further includes a plurality of LED light sources configured to contact the membrane in the oral cavity, and wherein the main body further includes an LED driving unit for driving at least one of the plurality of LED light sources.

12. The facial skin care device of claim 1, wherein the oral insertion module further includes a plurality of ultrasonic vibrators configured to contact the membrane in the oral cavity, and wherein the main body further includes an ultrasonic wave generation unit for generating ultrasonic waves through at least one of the plurality of ultrasonic vibrators.

13. A method of operating a facial skin care device comprising a main electrode, an auxiliary electrode that is separately provided from the main electrode, a plurality of oral electrodes, and a current generation unit for generating current connected to the main electrode, the method comprising:

disposing the main electrode and the auxiliary electrode on an outer surface of a facial skin;

disposing the plurality of oral electrodes on a membrane in an oral cavity;

receiving an input for selecting modes of operating the facial skin care device;

in response to a measurement mode being selected, flowing the current from the main electrode to the plurality of oral electrodes; and in response to a skin operation mode being selected, flowing the current from the main electrode to the auxiliary electrode.

14. The method of claim 13, further comprising:

in the measurement mode, measuring impedance between the main electrode and the plurality of oral electrodes;

connecting an oral electrode, among the plurality of oral electrodes, selected according to the measured impedance to the current generation unit; and flowing the current from the current generation unit to the connected oral electrode.

15. The method of claim 14, wherein the step of connecting the oral electrode includes:

selecting an oral electrode nearest or farthest to the main electrode or an oral electrode corresponding to a user-specified impedance among the plurality of oral electrodes, depending on the measured impedance.

16. The method of claim 13, further comprising:

in response to a whole operation mode being selected, connecting all of the plurality of oral electrodes to the current generation unit.

17. The method of claim 13, further comprising:

in response to a specific skin portion stimulation mode being selected, connecting at least one oral electrode adjacent to a user-specified specific skin portion among the plurality of oral electrodes to the current generation unit.

* * * * *